US006573110B1

(12) United States Patent
Hessler et al.

(10) Patent No.: US 6,573,110 B1
(45) Date of Patent: Jun. 3, 2003

(54) COMBINATORIAL CHEMISTRY SYSTEM AND METHOD OF USE

(75) Inventors: Robert J. Hessler, Stamford, CT (US); Robert Braun, Pennsylvania Furnace, PA (US); Nicholas Winograd, Spring Mills, PA (US)

(73) Assignee: The Penn State Research Foundation

( * ) Notice: Subject to any disclaimer, the term of this patent is extended or adjusted under 35 U.S.C. 154(b) by 0 days.

(21) Appl. No.: 09/674,900

(22) PCT Filed: Nov. 6, 1998

(86) PCT No.: PCT/US98/23697

§ 371 (c)(1),
(2), (4) Date: Dec. 15, 1999

(87) PCT Pub. No.: WO99/24834

PCT Pub. Date: May 20, 1999

Related U.S. Application Data

(60) Provisional application No. 60/064,708, filed on Nov. 7, 1997.

(51) Int. Cl.[7] ................ G01N 33/545; G01N 33/53; G01N 33/566; G01N 24/00; B01D 59/44
(52) U.S. Cl. .............. 436/531; 435/7.1; 435/7.2; 435/DIG. 14; 435/DIG. 15; 435/DIG. 16; 435/DIG. 17; 435/DIG. 18; 435/DIG. 19; 435/DIG. 20; 436/501; 436/518; 436/43; 436/173; 250/281; 250/282; 250/283; 250/284; 250/285; 250/286; 250/287; 250/288; 250/289; 250/290; 250/291; 250/292; 250/293; 250/294; 250/295; 250/296; 250/297; 250/298; 250/299; 250/300

(58) Field of Search .......... 435/7.1, 7.2, DIG. 14–20; 436/501, 518, 531, 43, 173; 250/281–300

(56) References Cited

U.S. PATENT DOCUMENTS

| 4,470,954 A | 9/1984 | Chiknas et al. |
| 4,977,077 A | 12/1990 | Ngo et al. |
| 5,639,603 A | * 6/1997 | Dower et al. ............ 435/6 |

FOREIGN PATENT DOCUMENTS

WO　　WO 95/25737　　* 9/1995

* cited by examiner

*Primary Examiner*—Maurie Baker
(74) *Attorney, Agent, or Firm*—Akerman Senterfitt; Stanley A. Kim

(57) ABSTRACT

A combinatorial chemistry system allows for the dual processing of different molecules coated on a library of beads. The system includes beads coated with different molecules on each bead, a bead holder, screening equipment and characterization equipment. Molecules on the beads are both screened and characterized simultaneously.

9 Claims, 4 Drawing Sheets

COMBINATORIAL CHEMISTRY SYSTEM AND METHOD OF USE

This application claims priority to U.S. Provisional Application No. 60/064,708 filed Nov. 7, 1997.

Combinatorial chemistry is a drug discovery technology being employed by pharmaceutical companies worldwide. Through combinatorial chemistry, a strategy of diversity is used to synthesize as many different molecules as possible and test their reaction to a specific "target", such as a disease or cell structure. Screening is the chemical assay of the molecules with the "target". If any of the molecule(s) show some reaction to the "target" during screening, the molecule(s) become a candidate for a commercial drug. The candidate molecule(s) are then characterized to determine both their composition and structure to enable additional synthesis and testing One technique of employing combinatorial chemistry utilizes polystyrene beads as a support structure for the molecules to be tested, The polystyrene beads are small, having diameters ranging from 1000 microns to less than 20 microns. Large numbers of polystyrene beads coated with members of a single class of compound, such as peptides, constitute a collection known as a library. Each library can include thousands of the beads with different molecules, yet each bead contains only a single type of molecule. Processing of the beads to test their reaction to specific "target" requires exposure to a bio reagent indicative of the "target". Each bead is screened to determine if there is any activity between the molecule(s) on the bead and the "target". Any activity between the molecule on a bead and the "target" is considered a "hit" and that molecule is further tested.

The usefulness of the bead technique is limited by the difficulty of manipulating individual beads, screening the molecules and then characterizing the "hits". Presently, a technique of electrospray mass spectrometry is utilized for characterizing the "hits", in which the characterization process can lake as long as 15 minutes to complete. Because the screening of a large library may result in the discovery of many thousands of possible "hits", the characterization of large libraries requires huge expenditures of time and labor. This has necessitated the use of smaller libraries, which do not take fill advantage of the combinatorial chemistry benefits.

Work by investigators has shown that beads can be characterized much more rapidly using Time-of-Flight/Secondary Ion Mass Spectrometry (TOF/SIMS). TOF/SIMS is another mass spectrometer technique. The TOF/SIMS reduces the time required for characterization of a single bead from 15 minutes to less than 1 seconds. However, the manual labor required to array the beads on a substrate after the screening process has been performed and also keep the beads positioned during the TOF/SIMS characterization has limited the usefulness of this technique.

It is an object of the present invention to provide a system and method to screen molecules on a library of beads, while also characterizing the molecules on the beads.

It is an object of the present invention to reduce the time it takes to screen and characterized molecules on a library of beads.

It is an object of the present invention to provide a bead holder to aid in the above-mentioned objects of the present invention.

SUMMARY OF THE INVENTION

The present invention is a combinatorial chemistry system and method of use for the dual processing of different molecules coated on a library of beads. The system includes beads coated with different molecules on each bead, a bead holder, screening equipment and characterization equipment. The bead holder retains the beads so that each of the beads has an exposed first section of the bead which is exposed independently of an exposed second section of the bead. The screening equipment and characterization equipment is used to assay and characterize the molecules on each bead. The method of use includes screening the exposed first section of the beads which are coated with molecules and characterizing the molecules located on the exposed second section of the beads. The method utilizes a library of the beads in the bead holder, whereby the bead holder retains the beads as described above. Included in the method is the screening of molecules on the beads, while allowing the characterization of the molecules on beads during the screening process.

DETAILED DESCRIPTION

The present invention provides a combinatorial chemistry system and method of use. The system includes a bead holder 10; equipment (not shown) for screening of molecules on polystyrene beads 12; and equipment (not shown) for characterization of molecules on the beads 12. The method takes advantage of the system by utilizing a dual process. The dual process allows the screening of the molecules on a library of the beads 12, while at the same time allowing the characterization of the molecules on each bead 12. The system and method reduces the time to screen and characterize molecules on beads 12 of a library, while taking advantage of the speed of equipment such as the TOF/SIMS.

Figure 1:
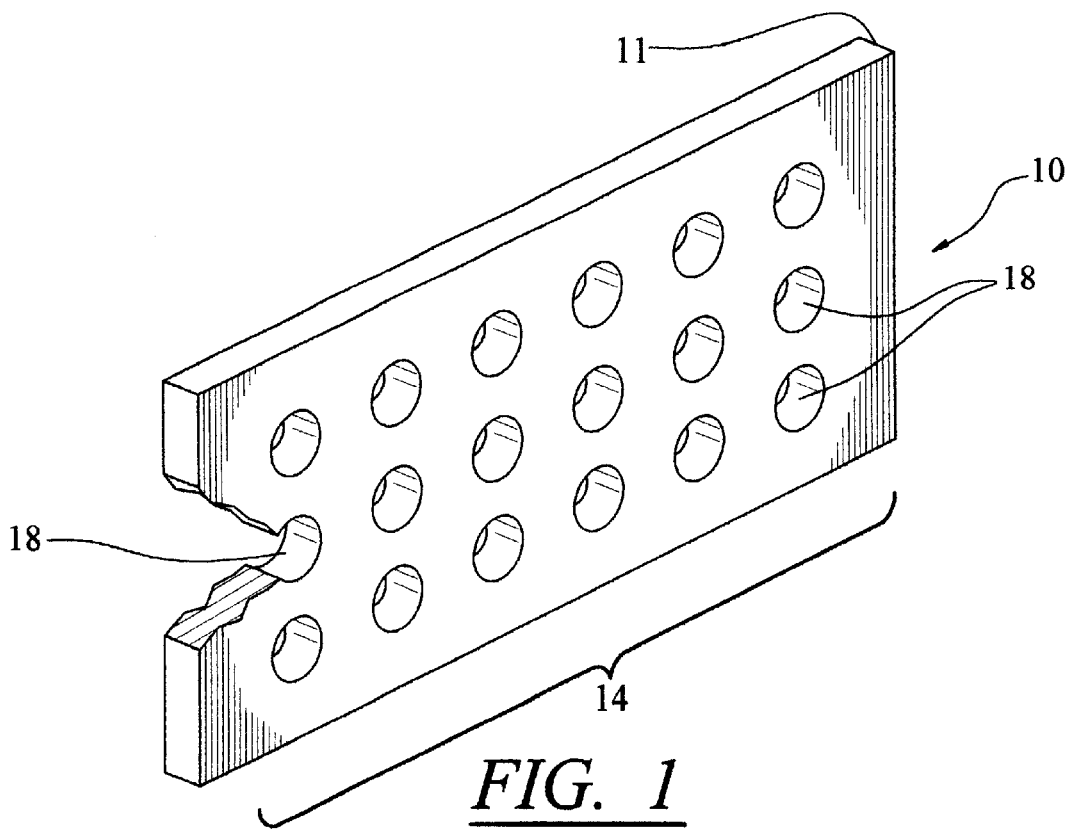
FIG. 1 is a perspective view of a bead holder according to the present invention.
Figure 2:
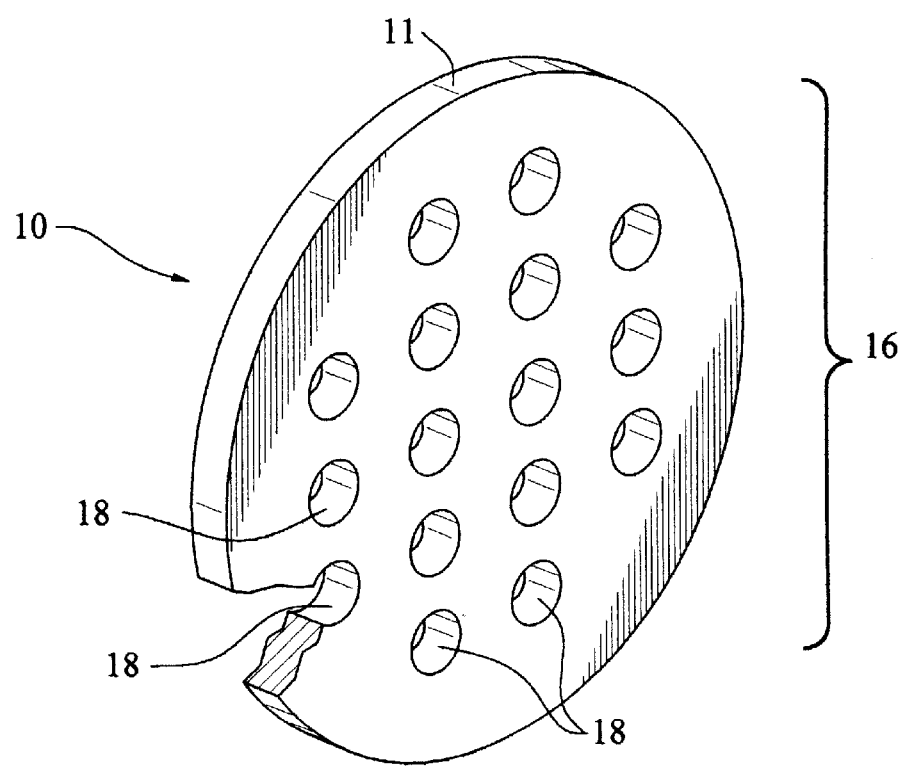
FIG. 2 is a perspective view of a bead holder according to the present invention.

The bead holder 10 of the system provides the exposure of two independent surface sections of the overall surface of each bead 12 held by the bead holder 10. The bead holder 10 is a plate 11 which includes holes 18 to receive the beads 12. The bead holder 10 can be of any geometric shape, such as a rectangle 14 or circle 16 shown in FIGS. 1–2. The amount and size of the holes 18 of the bead holders 10 shown in FIGS. 1–2 are for only illustrative purposes only. An actual bead holder 10 can be quite tiny and have many thousand of holes 18 for receiving the same number of beads 12. The number of beads 12 held by the bead holder 10 is only limited by the size of the holder 10 and the size of the beads 12. The holes 18 constrain each bead 12 to a specific location, but allow removal of the beads 12 for further evaluation and archiving if required. Production of the bead holder 10 utilizes semiconductor etching processes in order to form the holes 18 on a substrate. The thickness of the substrate depends upon the diameter of the bead 12 to be used. The usual materials for the substrate should be of a non-reactive material, such as a non-reactive metal. However, it is conceivable that the substrate could be fabricated from ceramic or glass. FIGS. 3–9 show cross-sectional views of different embodiments of the bead holder 10. Each of FIGS. 3–9 show only one hole 18 and bead 12 for illustrative purposes. The difference in the embodiments is the type of hole 18 in each bead holder 10. Each bead 12 positioned in the bead holder 10 includes an exposed top surface section 20 and exposed bottom surface section 22.

Figure 3:
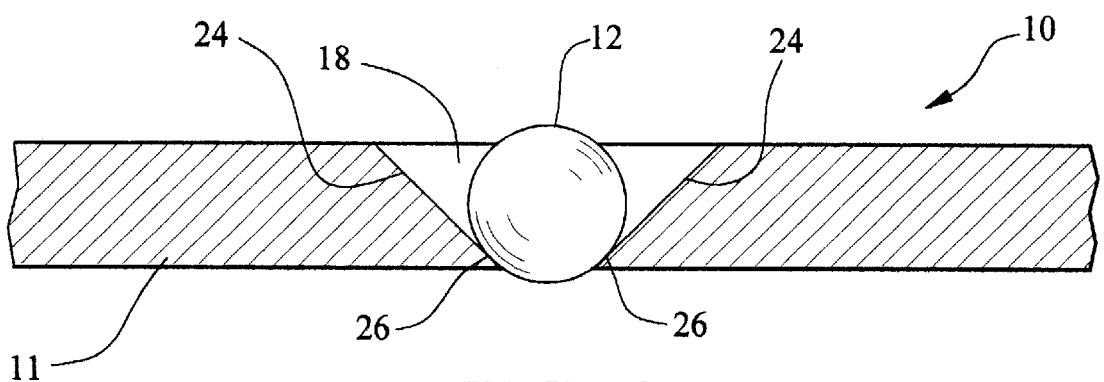
FIG. 3 is a cross-sectional view of a first embodiment of a bead holder according to the present invention.
Figure 4:
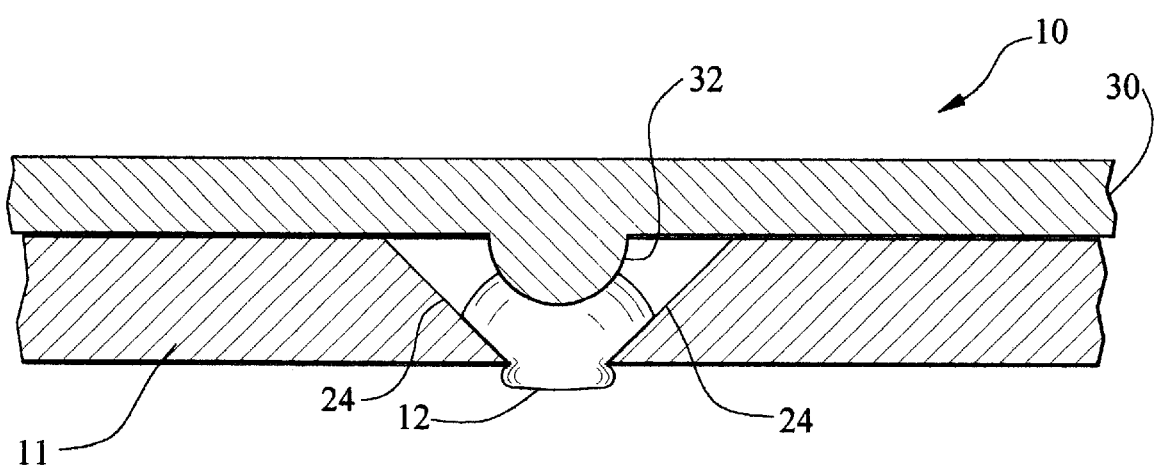
FIG. 4 is a cross-sectional view of a first embodiment of a bead holder according to the present invention.
Figure 5:
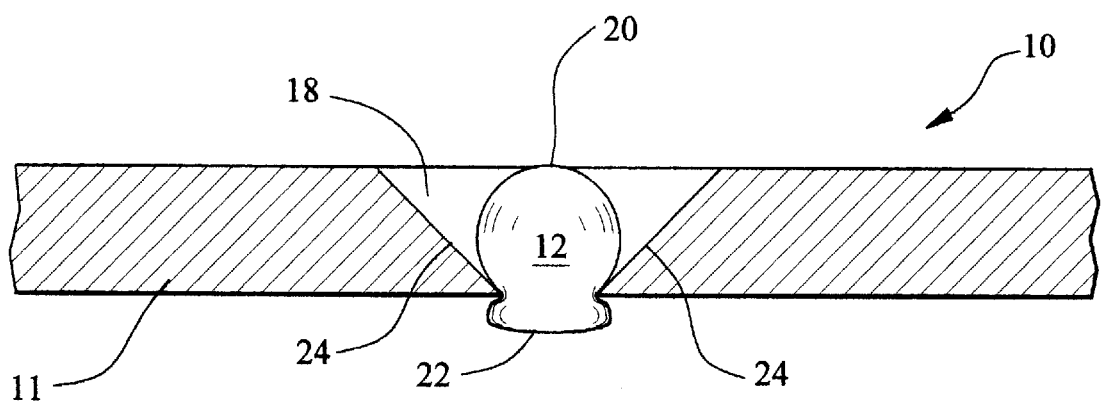
FIG. 5 is a cross-sectional view of a first embodiment of a bead holder according to the present invention.

FIGS. 3–5 show a first embodiment of the bead holder 10. The holes 18 of the bead holder 10 of the first embodiment include slanted sides 24 which slant away from each other starting at the bottom 26 of the holes 18. To insert the heads 12 into the holes 18, more heads 12 then holes 18 are layered on a top surface 28 of the bead holder 10 until all of the holes 18 are filled. A vacuum can be additionally applied from below the holes 18 to cause air or liquid to flow through the holes 18 and pull the beads 12 into each hole 18. The vacuum can also aid in retaining the beads 12 in the holes 18. After all the holes 18 have been occupied, the excess beads 12 are removed with either a rinse, a vacuum chuck or a mechanical brush. A plate 30 is then placed on top of the bead holder 10, as shown in FIG. 4. The plate 30 can be flat (not shown) or have dimples 32 which are aligned to match the holes 18 of the bead holder 10. The size and shape of the dimples 32, depends upon the diameter of the beads 12 used. Pressure is applied from above to either type of plate 30 The pressure from the plate 30 against the beads 12 forces the beads 12 to partially extrude and deform through the holes 18 of the bead holder 10, as shown in FIG. 5. After the plate 30 is removed, the beads 12 are retained by the holes 18 due to a pressure fit.

Figure 6:
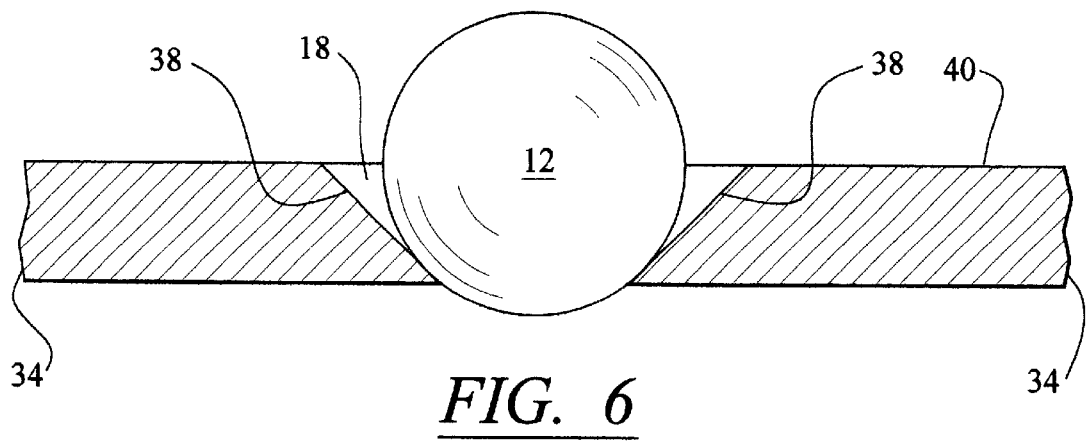
FIG. 6 is a cross-sectional view of a second embodiment of a bead holder according to the present invention.
Figure 7:
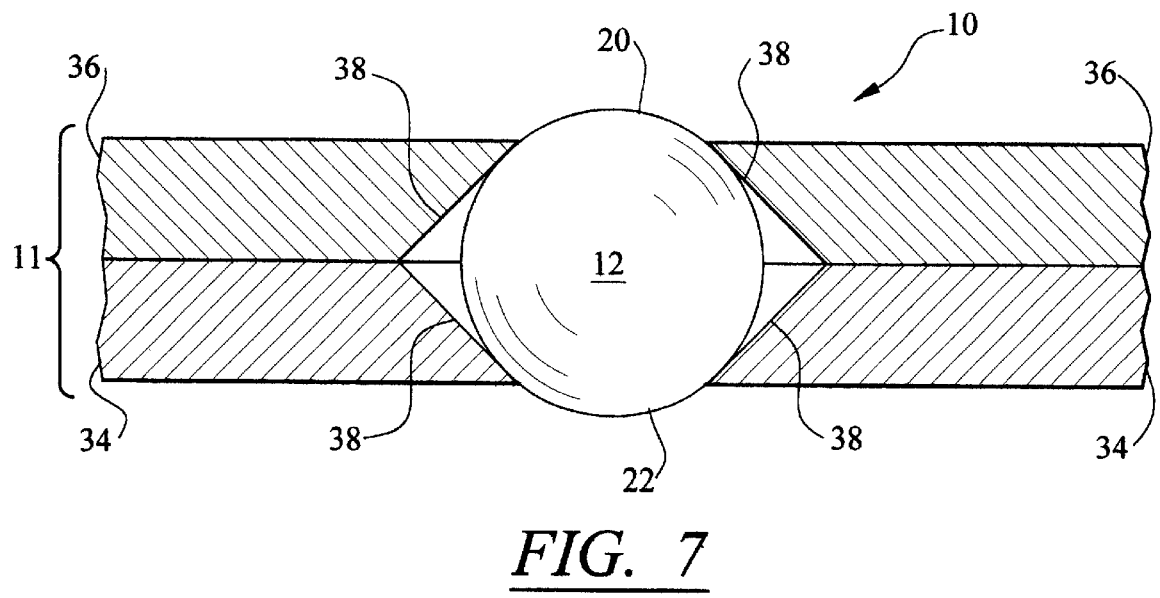
FIG. 7 is a cross-sectional view of a second embodiment of a bead holder according to the present invention.

A second embodiment of the bead holder 10 is shown in FIGS. 6–7. The second embodiment uses a two piece substrate construction of a bottom layer 34 and top layer 36. Each layer 34, 36 has a set of holes 18 which align with each other when the two layers 34, 36 are place together. Unlike the first embodiments, the second embodiment retains the beads 12 without forcing the beads 12 to change shape. The shape of the sides 38 of the holes 18 in each layer 34, 36 are for locking the beads 12 in place. Most any geometric shape for the sides 38 can be used, as long as the sides 38 of both layers 34, 36 lock the beads 18 in place. FIGS. 6–7 show the sides 38 slanted as an example. To insert the beads 12 in the holes 18, more beads 12 then holes 18 are layered on a top surface 40 of the bottom layer 34 until all of the holes 18 are filled. A vacuum can be additionally applied from below the holes 18 of the bottom layer 34 to cause air or liquid to flow through the holes 18 and pull the beads 12 into each hole 18. The vacuum can also aid in retaining the beads 12 in the holes 18. After all the holes 18 of the bottom layer 34 have been occupied, the excess beads 12 are removed with either a rinse, a vacuum chuck or a mechanical brush. Next, the top layer 36 is aligned over the bottom layer 34 in order to trap the beads 12, as shown in FIG. 7. The bottom and top layers 34, 36 are either bonded together using adhesive or, if there is the possibility of needing to retrieve the beads 12, the layers 34, 36 can be held together by a clamping fixture (not shown).

Figure 8:
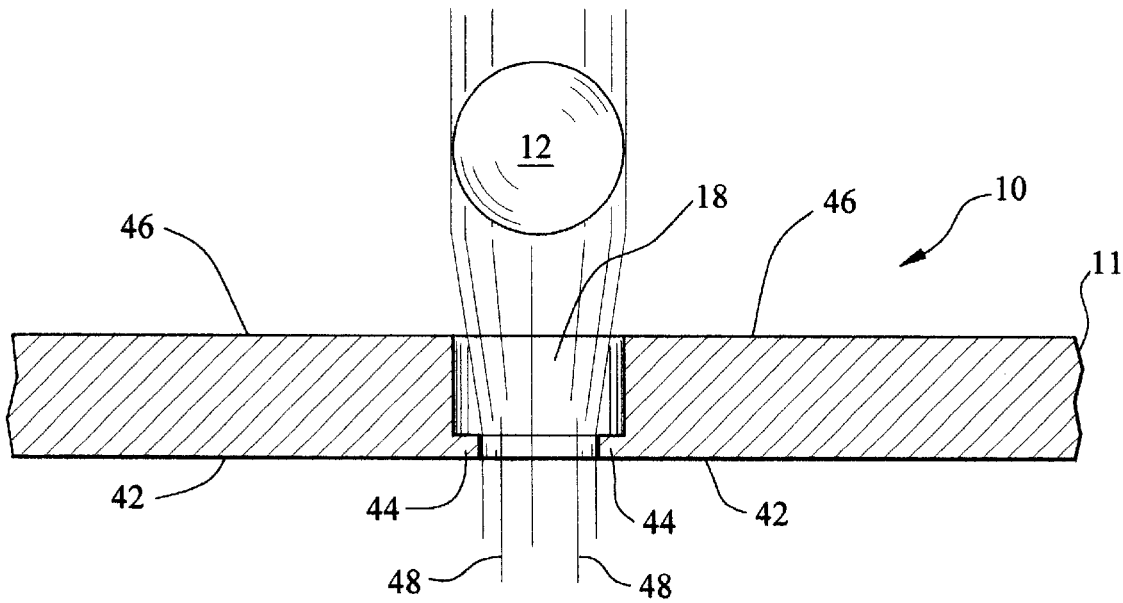
FIG. 8 is a cross-sectional view of a third embodiment of a bead holder according to the present invention.
Figure 9:
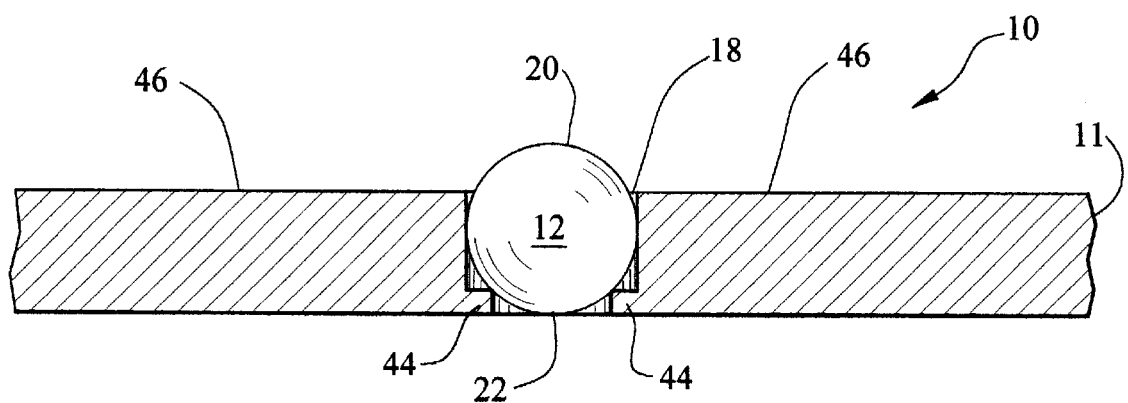
FIG. 9 is a cross-sectional view of a third embodiment of a bead holder according to the present invention.

FIGS. 8–9 show a third embodiment of the bead holder 10. The third embodiment of the bead holder 10 includes holes 18 which are of a diameter that are slightly less than the diameter of the beads 12. As shown in FIGS. 8–9, the third embodiment includes a reduction in diameter of the holes 18 near a bottom surface 42 of the bead holder 10, which forms a lip 44. The beads 12 are inserted into the holes 18 from a top surface 46 of the bead holder 10. First, more beads 12 then holes 18 are forced towards the holes 18 in a contained environment until all of the holes 18 are filled. The beads 12 can be forced into the holes 18 using a stream 48 from either an air stream from above the holes 18, a liquid stream from above the holes 18 or a vacuum applied from below the holes 18, as shown in FIG. 8 The lip 44 acts as a stop to restrain the beads 12 from passing through the holes 18. After all the holes 18 have been occupied, the excess beads 12 are removed with either a rinse, a vacuum chuck or a mechanical brush. The beads 12 are retained by the holes 18 due to a pressure fit.

The method of using the system allows use of combinatorial chemistry techniques to reduce the time to screen and characterize molecules on each bead 12 of a library. The method employs the dual process of screening the molecules on one side of the bead holder 10 and at the same time characterizing molecules on the other side of the bead holder 10. For example, molecules on the exposed bottom surface section 20 of each bead 12 in the bead holder 10 can be screened. At the same time that the bottom surface section 20 is being screened molecules on the top surface section 22 of each bead 12 can be characterized. Assay equipment known in the art is used to perform the screening and characterization equipment known in the art is used to perform the characterization process. The method allows the use of larger libraries of beads 12 and takes advantage of equipment like the TOF/SIMS. A computer and software can be utilized to control when to screen the molecules on the beads 12; when to characterize the molecules on the beads 12; and whether to characterize the molecules on all of the beads 12 or just the beads 12 with "hits". The combination of the method of use of the system's bead holder 10 and computerization allows the user to take full advantage of the combinatorial chemistry benefits. This method is also desirable because the assaying of beads 12 can cause chemical contamination of the beads 12. Contamination of beads 12 can complicate the characterization procedure. The bead holder 10 of the present invention aids in preventing contamination of part of the bead 12, so that the molecule(s) on the bead 12 can be characterized.

While different embodiments of the invention has been described in detail herein, it will be appreciated by those skilled in the an that various modifications and alternatives to the embodiments could be developed in light of the overall teachings of the disclosure. Accordingly, the particular arrangements are illustrative only and are not limiting as to the scope of the invention which is to be given the fill breadth of the appended claims and any and all equivalents thereof.

We claim:

1. A combinatorial chemistry method comprising the steps of:
   (A) providing a library comprising at least one bead coated with molecules, the at least one bead having a first section and a section, the molecules in each section having the same chemical structure;
   (B) providing a bead holder to retain the at least one bead, wherein the bead holder retains the at least one bead so that the first section and second section are exposed;
   (C) placing the at least one bead in the bead holder, the first section being exposed independently of the second section while the bead is in the bead holder so that the processing of one of said sections does not affect the other section; and (D) while the bead is retained in the bead holder, screening the molecules located on the first section of the at least one bead of the library; and (E) while the bead is retained in the bead holder, characterizing the molecules located on the second section of the at least one bead of the library.

2. The method of claim 1, wherein the at least one bead comprises polystyrene.

3. The method of claim 1, wherein the library comprises a first bead coated with molecules and a second bead coated with molecules, wherein the molecules on said bead have a different chemical structure than those on said first bead.

4. The method of claim 1, wherein the molecules coating the at least one bead are peptides having the same chemical structure.

5. The method of claim 1, wherein the bead holder is a plate which includes holes to retain the beads.

6. The method of claim 5, wherein the at least one bead is loaded into the bead holder using a fluid stream to force the at least one bead into the holes.

7. The method of claim 1, wherein the screening of the molecules located on the first section of the at least one bead does not interfere with the characterization of the molecules located on the second section of the least one bead.

8. The method of claim 1, wherein the characterization of the molecules located on the second section of the at least one bead is performed by Time-of-Flight/Secondary Ion Mass Spectrometry.

9. The method of claim 1, wherein a computer controls the simultaneous screening and characterization of the molecules located on the first and second sections of the at least one bead.

* * * * *